(12) United States Patent
Romier

(10) Patent No.: US 9,972,058 B2
(45) Date of Patent: *May 15, 2018

(54) METHOD FOR CORRECTING THE TIME DELAY IN MEASURING AGRICULTURAL YIELD

(71) Applicant: GEOSYS SAS, Balma (FR)

(72) Inventor: Chloe Romier, Toulouse (FR)

(73) Assignee: GEOSYS SAS, Balma (FR)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/463,442

(22) Filed: Mar. 20, 2017

(65) Prior Publication Data

US 2017/0193613 A1    Jul. 6, 2017

Related U.S. Application Data

(63) Continuation of application No. 14/129,274, filed as application No. PCT/EP2012/062380 on Jun. 26, 2012, now Pat. No. 9,600,846.

(30) Foreign Application Priority Data

Jun. 29, 2011   (FR) ...................................... 11 55833

(51) Int. Cl.
  *G01V 3/38*     (2006.01)
  *G06Q 50/02*    (2012.01)
  *G01N 33/00*    (2006.01)

(52) U.S. Cl.
  CPC ......... *G06Q 50/02* (2013.01); *G01N 33/0098* (2013.01)

(58) Field of Classification Search
  CPC .... G06F 3/04883; G06F 1/3203; G06F 21/36; G06F 3/04842; G06F 17/3002; G06F 17/3053; G06F 17/30896; G06F 17/30905; G06F 3/011; G06F 3/0482; G06F 17/30702; G06F 21/31; G06F 2203/04808

See application file for complete search history.

(56) References Cited

U.S. PATENT DOCUMENTS

| | | |
|---|---|---|
| 5,995,895 A | 11/1999 | Watt et al. |
| 6,119,531 A | 9/2000 | Wendte et al. |
| 9,600,846 B2 * | 3/2017 | Romier ................ A01B 79/005 |

FOREIGN PATENT DOCUMENTS

DE    10 2005 000770 B3    7/2006

* cited by examiner

*Primary Examiner* — Roy Y Yi
(74) *Attorney, Agent, or Firm* — Dorsey & Whitney LLP

(57) ABSTRACT

The invention relates to a method of processing a set of data collected by at least one sensor at successive points on the travel over a plot of land (1), by at least one vehicle (2), each one of the said pieces of data having been recorded with a time difference in relation to the moment of the vehicle passing over a given point on the plot, i.e. representing information relating to the state of the vehicle at a moment prior to its moment of recording, each piece of data being associated with a moment of recording and a geographical position of a point known as the measuring point at this moment of recording, supplied by geolocation means.

The method comprises a phase of estimating an optimum difference value by minimizing a degree of projection of a three-dimensional map of values measured at each geographical point, and correction of the data measured from this difference.

22 Claims, 5 Drawing Sheets

METHOD FOR CORRECTING THE TIME DELAY IN MEASURING AGRICULTURAL YIELD

CROSS-REFERENCE TO RELATED APPLICATIONS

This application is a continuation of U.S. application Ser. No. 14/129,274 filed Dec. 24, 2013, issued as U.S. Pat. No. 9,600,846 on Mar. 21, 2017, which is a 371 application of international application No. PCT/EP2012/062380 filed on Jun. 26, 2012, which claims priority to French Application No. 1155833 filed on Jun. 29, 2011, the contents of each of which are herein incorporated by reference in their entirety.

The present invention relates to the area of farming, and more specifically to precision farming. It relates more precisely to a method of correcting time difference in measurements, preferentially measurements of flows of grain, and creating yield maps reflecting reality.

BACKGROUND OF THE INVENTION

In farming, the various products provided for the land and crops are called "inputs". These products can be, for example, a seed, a fertilizer, a pesticide or irrigation water. In a same farming plot, the inputting needs differ geographically, for example according to the exposure of each area, or according to the local slope etc.

In conventional farming, the provision of inputs on a farming plot is made without taking into account the variabilities inside this plot. On the other hand, precision farming consists of taking into account the variability inside a farming plot, in such a way as to optimize the quantity of inputs applied. It is understood therefore that the quantity of inputs to apply will be managed, in precision farming, in accordance with the needs of each area of a farming plot, rather than to apply a model established according to an average over the total area of the said farming plot.

As the population is being more and more demanding towards the farming profession in terms of quality, traceability and impact on the environment, precision farming has come into existence in order to answer this demand on the one hand, and on the other hand to reduce farming costs by improving the effectiveness of the inputs.

The variabilities within a farming plot are taken into account using maps, known as "yield maps", which state the real production observed at each point of each plot, for example in the form of grain mass harvested at this point.

Today, farming equipment, for example a combine harvester, usually includes a sensor set, for example, flow sensors (pressure, optical density etc), moisture, etc, and a geolocation system, for example GPS. These sensors transmit measurements, stored in a file, aiming to be able to calculate yields at each point, these measurements can be, for example, a value relating to a flow passing at each moment through the machine, which, associated with a geolocation, constitute a set of data.

This set of data defines a flow map. The file also contains values of instantaneous yield, obtained by calculation using the instantaneous cutting width. This instantaneous yield value data is sometimes assimilated to a yield map.

However, this data includes errors related to various phenomena, for example maneuvers carried out during harvesting, of which there are various sources:

the combine harvester is completely full,
the combine harvester is stationed to empty its load of grain,
the combine harvester rotates at the end of the row,
the farming plot is sloping,
the weather changes the weight of grain observed,
the imprecision of the cutting width used,
the time lag,
the loss of GPS signal,
the blockages and/or loss of grain in the combine harvester,
the precision of the sensors.

Some of these errors are known, but correcting them remains difficult. For example, the time lag corresponds to the time interval between the time where the crop is cut at the front of the machine and the time where the grain passes in front of the flow sensor. These time lag values change in accordance with working conditions and the crop. The correction of these time lag values is predefined on leaving the factory, but most manufacturers allow the operator to change this time lag.

Cartography software which refines instant yield data is already available, for example by filtering extreme values in order to correct the data of these maps, which is, in general, assimilated to yields.

In the current state of the art, these corrections are inadequate, and a farming producer who manages a farming plot in precision farming must correct the yield map supplied by the cartography software that he uses, based on his own knowledge of the farming plot. The time spent achieving this correction is considerable, and the result still includes errors. Moreover, this data calculated from instantaneous yield, being in the current state of the art and of the market, directly assimilated to yield data, the final map cannot show the variability of the yield in a very true way.

OBJECT AND SUMMARY OF THE INVENTION

The invention therefore relates to a system and a method which allow the very effective correction of data coming from sensors, and then the building of yield maps by using this corrected data, this being done in an automated way.

More precisely, the invention initially relates to a method of processing a set of data, collected by at least one sensor at successive points on the travel over a plot of land by at least one vehicle, each one of the said pieces of data having been recorded with a time difference in relation to the moment of the vehicle passing a given point of the plot, that is, representing information relating to the state of the vehicle at a moment prior or subsequent to its moment of recording, each piece of data being associated with a moment of recording and with a geographical position of a point, known as the measuring point, at this moment of recording, supplied by means of geolocation.

The method includes a phase 200 of correcting the time difference, including the following steps:

step 210—of generating a set of data adjusted for each time lag value, amongst a set of values of time lags to test, by shifting, for each piece of data associated with a measuring point, the geographic coordinates of this measuring point, in accordance with the chosen difference, by replacing the geographic coordinates of this measuring point by the geographic coordinates of the previous (or future) measuring point with a given time lag. This can also be carried out by shifting the values recorded by the various sensors from one measuring point to another.

step 230: then, for each set of adjusted data thus created:
of building a three-dimensional map, showing, for a selection of measuring points, their latitude and longitude and a height, known as the sensor value, for example a flow (for example a mass flow) or a yield, in accordance with the data associated with this measuring point, along the X, Y and Z axes respectively, of determining a measurement of the developed surface area of the three-dimensional map, of calculating the surface area of the projection of the three-dimensional map onto the plane of latitudes and longitudes, of calculating a ratio, known as the projection ratio, between the developed surface area of the three-dimensional map and the area of projection, step 240: then determining the minimum value of this projection ratio for all the sets of adjusted data associated with all the values of time lags to test, the said minimum value corresponding to a value known as the optimum time difference value, and correcting the set of data by using this optimum time difference value.

In a preferred implementation, the method includes, in addition, a step 220 of selecting, in each set of adjusted data, measuring points constituted of measuring points known as "normal", positioned on rows of lines, substantially straight and parallel to each other, the measuring points located at the start and end of the rows, at half-turns, as well as measuring points constituting the identification of plots being excluded from the set of normal measuring points.

Preferentially, the normal measuring points are projected onto a regular-mesh grid, the associated data being interpolated by linear regression. In this way, the measuring points are associated with meshes with the same area, which facilitates the later comparison of data measured.

According to another implementation, possibly used in conjunction with previous ones, the method includes, in addition, a step 250, of filtering corrected data by using the optimum time difference value, said filtering including:

the elimination, in the corrected data, of points which have a flow value equal to 0, or according to the data used, a yield value equal to 0.

the calculation of the average M of the remaining flow measurements (that is, the measuring points with zero corrected data excluded), or according to the data used, of the remaining yield data, the calculation of the standard deviation EC of remaining flow data, or according to the data used, of the remaining yield data, and the elimination of all measuring points having an absolute flow or yield value higher than the absolute value of the average M with addition of k times the standard deviation EC for the flow or yield data respectively.

In this case, preferentially, k is chosen quite high so that extremes are removed. The inventors have observed, for example, that the value 3 produced an effective filtering of data.

According to another implementation, the yield map is optionally built, in conjunction with the previous steps, according to the method which includes, in addition:

a step 510 of distributing the value of the measurement data over the space covered by the width of the equipment, a step 520, wherein:

a grid, of predetermined mesh, is applied on the plot of land 1, and the corrected flow data measured inside each cell are added up, for the cells at the plot edge, the percentage of area occupied by the plot of and is defined, the corrected flow data associated with all the points contained in each cell are added up, this sum is divided by the area of each cell to obtain a yield value associated with each cell.

This arrangement allows the creation of a yield map from the corrected flow data.

In an advantageous implementation, the method includes, in addition, a phase 400, of creating a contour, called the harvested plot contour, obtained by tracing an area known as the predetermined buffer radius around each measuring point, then merging all the buffers to obtain this harvested plot contour, and in that; for each cell at the plot edge, the percentage of area occupied by the plot of land is calculated as the intersection of the harvested plot contour with the cell edges.

In a specific application, the data are measurements of grain weights, these measurements being weighted by the total weight of grain harvested on the plot.

The invention relates in another aspect to a farming plot management system, the system including a data recovery machine, suitable for travelling along a plot of land, the said recovery machine including a set of sensors the moment of measurement of which can have a time lag in relation to the moment of the machine passing a given point of a plot of land, a geographical positioning system of a predetermined precision, calculation means suitable for receiving data collected by the set of sensors, said calculation means including means of implementing a method as disclosed.

BRIEF DESCRIPTION OF THE FIGURES

The features and advantages of the invention will be better appreciated from the description which follows, the description disclosing the features of the invention through a non-exhaustive example of application.

The description is based on the accompanying figures, which show.

DETAILED DESCRIPTION OF AN EMBODIMENT OF THE INVENTION

Figure 1:
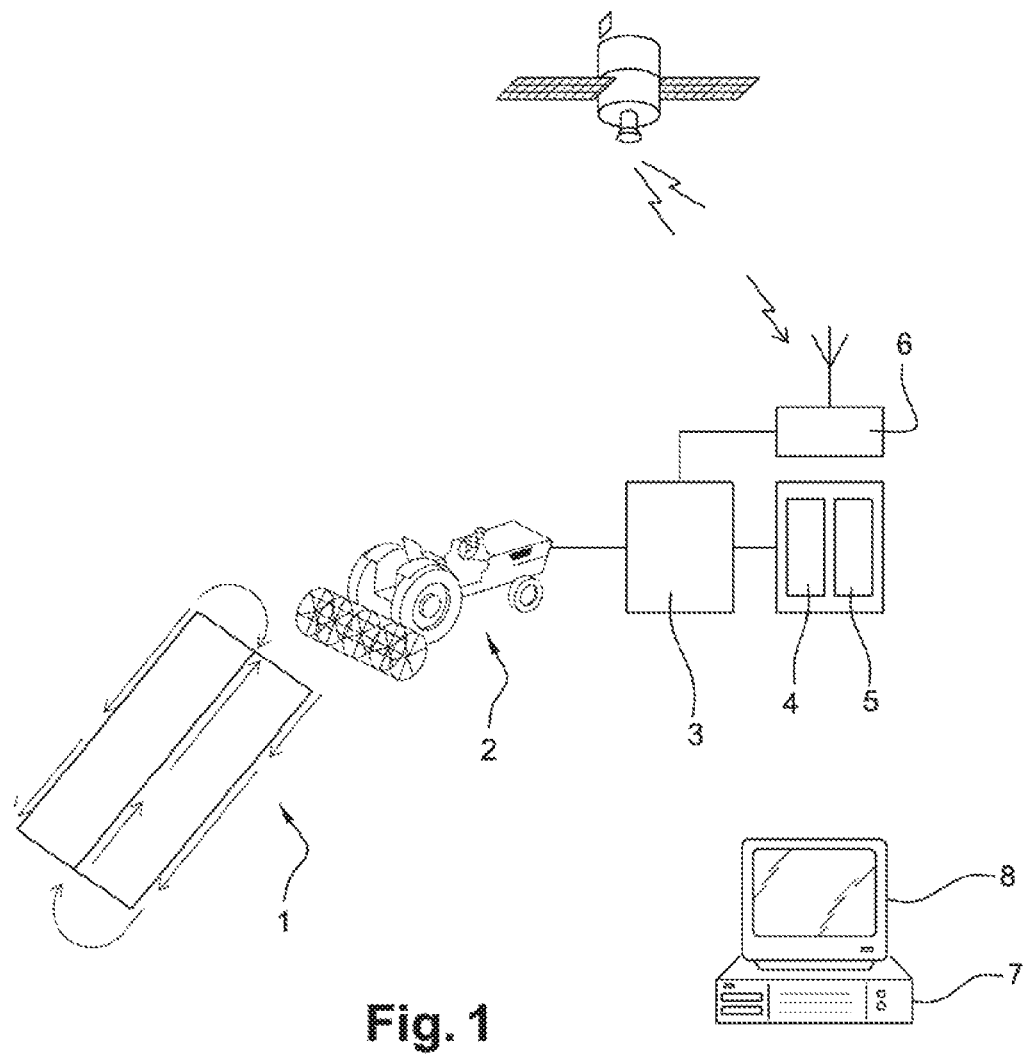
FIG. 1: a diagram of the elements included in the invention.

The invention finds its place in the context of a farm. The case of a farmer is considered, who needs a yield map in order to optimize the management of a farming plot.

This farmer uses, to cultivate his plot of land 1, a farming machine 2, which is, in the present example, no way exhaustive, a combine harvester. Conventionally, the combine harvester 2 sweeps along the plot of land 1 according to a preferential path, with half-turns at each end of said plot of land 1.

This combine harvester 2 is equipped here with a device 3 for taking measurements, connected to a set of sensors which includes, for example, a grain flow sensor 4 and a moisture sensor 5. The combine harvester 2 includes, moreover, a global positioning system 6, for example, GPS, also connected to the device for taking measurements 3.

This device for taking measurements 3 is used for acquiring data from the sensors 4, 5 and from the positioning system 6 at regular intervals, for example, every second, and to store them in the form of raw data files. The device 3 for taking measurements is typically a microcomputer of the so-called PC type, equipped with a display interface, indicating to the operator of the combine harvester 2 the grain mass already harvested, or other parameters.

These raw data files, stored in the memories of the device for taking measurements or transferred by way of telecommunication onto a remote computer system, optionally contain data relating to several farming plots, several crops, and sometimes several years. They are formatted according to a format compatible with the device 3 used for taking measurements.

The device 3 for taking measurements supplies raw data files according to a specific data storage format, said format being the owner (belonging to a private entity) or not, and using a type of binary or text encoding or another, this specific format and this type of encoding being chosen by the manufacturer of the device 3 for taking measurements.

The device according to the invention includes, moreover, an analysis device 7, here of the microcomputer type, having means of entering raw data collected from the files by the device for taking measurements, means of calculating based on these raw data files, means of storing calculated results, and means 8 of displaying a yield map from the calculations carried out. This analysis device 7 advantageously includes a user interface, and means of transmitting data via a network of a type known per se.

In one embodiment, the analysis device 7 is installed independently of the farming machine, in a place where the collected data are analyzed.

In one specific case of embodiment, this analysis device 7 is suitable for processing data coming from multiple farming machines working on the same plot of land 1 or on various plots.

Figure 2:
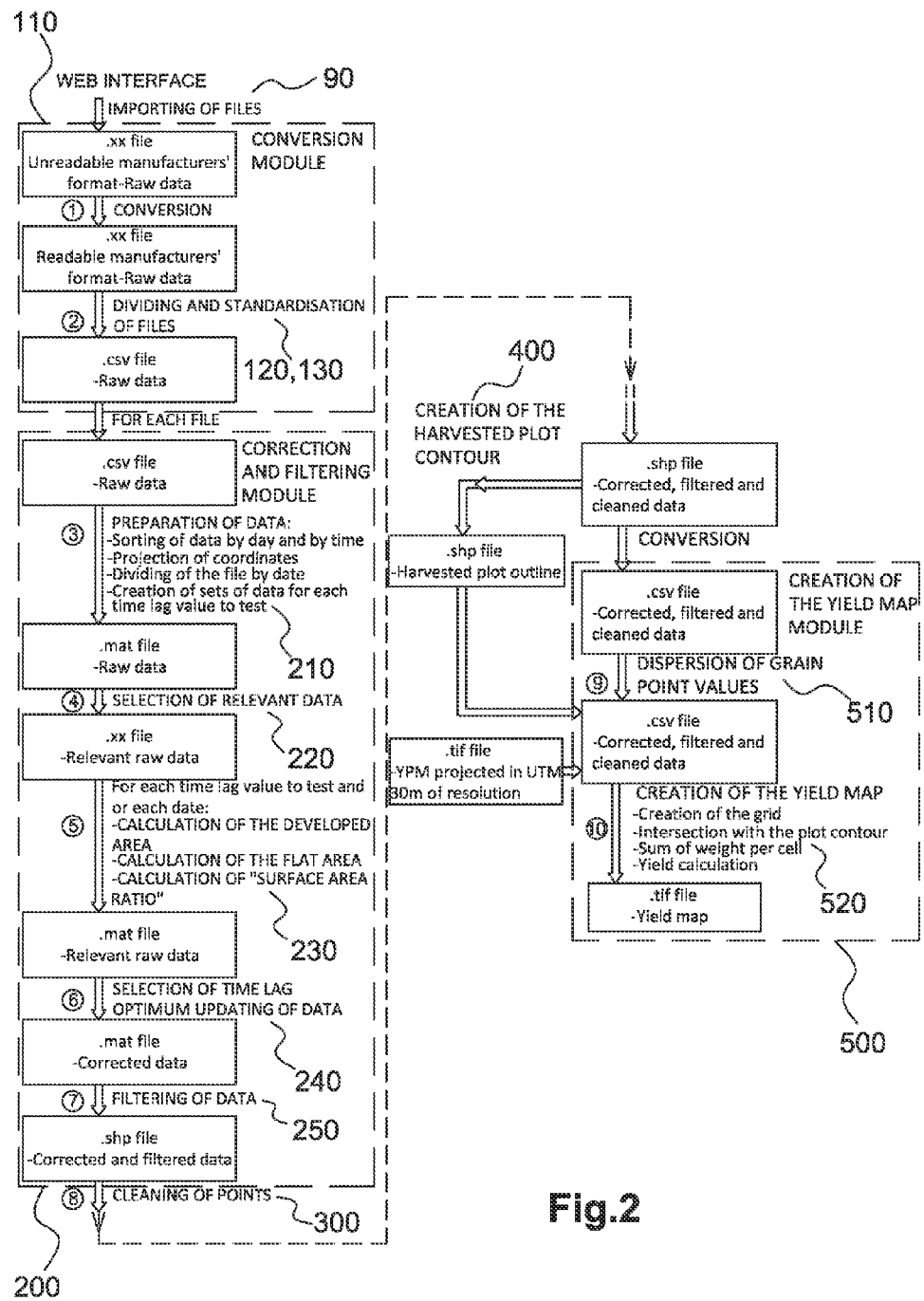
FIG. 2: a flow diagram of the main steps of a way of implementing a method according to the invention.

FIG. 2 thus illustrates a method of processing data collected by the sensors of at least one farming machine. Preferentially, this method is implemented after a plot has been totally swept by the farming machine, for example after complete harvesting of the said plot.

In a phase 90 preliminary to the method, the raw data collected during the passing of the combine harvester 2 over the plot of land 1 has been imported into the analysis device 7.

As is shown in FIG. 2, a method according to the invention initially includes a first phase 100, known as the "conversion phase", which consists of building from raw data files, collected by data sensors (or calculated, such as instantaneous yield), a set of usable data files, namely pre-processed data.

A first step 110 of this conversion phase 100 consists of translating each one of the raw data files into a formatted raw data file in a standard format, said file then being known as the "formatted data file".

According to a preferred embodiment, step 110 is carried out using software available on the market. This software supplies raw data files formatted into a standard format having a .csv or .shp type extension. The .shp file format ("shape format") relates to the area of geographical information systems.

It will be understood that the advantage of this embodiment is that it allows the standardization of data following processing.

A second step 120 of the conversion phase 100 consists of creating one file of usable data per plot, known as the "plot file". During this step 120, the raw data files are processed so that each one of the usable data files, known as plot files, only include information connected to a single farming plot, a single crop and a single crop cycle.

More precisely, in the step 120, a file of formatted data is divided up to extract a set of points known as "measuring points", each one of these measuring points being associated with a set of collected data, relating to one plot, one crop and one crop cycle (generally one year).

The unit of each piece of relevant data is standardized according to the type of data. This is because the data available in the formatted data files, as well as their units, depend on the equipment used, and are not all required for building a yield map.

In the present example embodiment, particularly the following information is adapted as so-called "relevant data" for each measuring point: longitude of the measuring point, latitude of the measuring point, altitude of the measuring point, height of the cut, width of the cut, moisture level of the harvested material, flow of harvested material, date, time. It will be understood that, in this sense, a measuring point is a geographical point determined by its coordinates from the GPS positioning system 6, and that the relevant data are data from the sensors 4, 5, collected at the moment of the passing of the combine harvester 2 over this geographical point. The set of data adapted can be upgradeable, and can particularly comprise of instantaneous-yield values.

A plot file thus includes a set of measuring points each of which has relevant data associated with it, as defined above. It will be understood that the geometric distribution of these measuring points is known through the relevant data relating to the location of the measuring point, and that this geometric distribution is not necessarily homogeneous, particularly because of the changes in direction of the combine harvester 2, and the traces carried out by this combine harvester 2 on the plot of land 1 not being parallel.

An optional step 130 can thus be carried out following step 120. It consists of weighting the flow values, measured at each measuring point, in accordance with the total weight actually harvested on the plot.

This step 130 requires knowing the real weight of all of the crop. This real weight of all of the crop is, in general, known to the farmer when weighing it on a set of scales. This real weight, referred to as "weighed quantity", allows the calculation in step 130 of a correction to each one of the weight values measured at each measuring point 10, this correction being calculated by the following formula:

$$\text{Correction} = \frac{\sum \text{basic weight} - \text{Weighed quantity}}{\text{Weighed quantity}}$$

Thus the corrected flow values are obtained at each point, relating to the whole plot of land. The corrected flow can be shown, for example, in the form of the percentage of the total weight harvested per unit of time.

The relevant data associated with the measuring points for each plot file, namely relating to one plot, one crop and one crop season, thus form a "usable data file", associated with this plot of land 1, this crop and this season.

The method according to the invention then includes a second phase 200, known as the "correction of difference phase". This phase 200 uses, at the start, a usable data file, as previously defined.

A "time lag" was defined previously, for good understanding following the description, denoted "t_lag" in the remainder of the description, as being equal to the interval of time between the moment where the crop is cut at a physical cutting point, at the front of the combine harvester 2 used, and the moment where the crop passes the flow sensor 4.

This time lag t_lag changes in accordance with the working conditions. For example, the intensity of the flow, the properties of the crop harvested, the slope on which the combine harvester 2 maneuvers, are factors which can affect the flow measured.

In practice, this indicates that the flow measurement transmitted by the flow sensor 4 and the moisture measurement transmitted by the moisture sensor 5 and sensed by these sensors at a moment "t" correspond, in reality, to a plant cut by the combine harvester 2 at a moment t1=t−t_lag.

This time lag is, in general, between ten and fifteen seconds.

It is specific to the type of combine harvester 2 used, and to the date of work, particularly influenced by weather conditions.

This time lag is also influenced by the crop, according to whether the crop is dry, such as wheat or rape, or moist crops. This time lag is predefined in the factory where the farming machine used is manufactured, but can also be changed by an operator. However, it is observed that this predefined or changed time lag is often not very precise, the imprecision being able to be as much as several seconds.

An error on the estimation of the time lag value naturally affects the accuracy of the yield map to be built, such a map being achieved by correcting the predefined time lag, influencing the data from the sensors.

The effect of this time lag on the correct association of measurements from the sensors 4, 5 at each position of the measuring point can be illustrated by an example. A combine harvester 2 which passes over a footpath and therefore temporarily harvests no grain flow, is considered.

If the time lag value is overestimated in relation to its true value, the measuring points associated with a grain flow of zero value will be shifted too much backwards in time, and positioned on the map of the plot of land 1 in front of the footpath in the direction the combine harvester 2 is moving.

If, on the other hand, the time lag value is underestimated in relation to its true value, the measuring points associated with a zero grain flow will be too little shifted back in time, and thus positioned on the map of the plot behind the path.

If, finally, the time lag value is correctly estimated in relation to its true value, the measuring points associated with a zero grain flow will be situated on the map of the plot exactly on the footpath.

Figure 3:
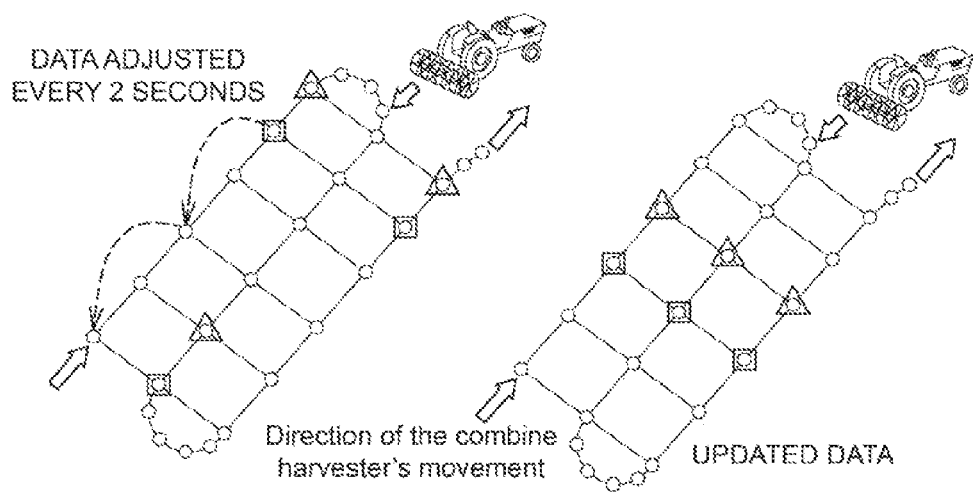
FIG. 3: a diagram illustrating the principle of adjusting data.

Moreover, while the combine harvester 2 goes backwards and forwards on the plot of land 1, the differences give opposing positioning errors, which mount up to make the yield map incorrect (see FIG. 3 which illustrates as an example an adjustment of the data by two seconds). An adjustment of these data according to a correct estimation of the time lag re-establishes the continuity of the measurements in two dimensions.

The prime purpose of the second phase 200 is thus to estimate the time lag in an optimal way.

This second phase 200 is broken down into several steps.

In a first step 210, a set of data known as adjusted data is created.

According to a preferred embodiment, the steps are amongst the following:

First of all, the data from the plot file are sorted (associated with one plot, one crop and one crop season), by day and by time.

Then the GPS (or another positioning system) positioning data collected from the positioning sensor 6 are projected (or not) into UTM (Universal Transverse Mercator) type data, or any other type of projection, in order to show it on a map.

This is because the raw location data supplied by the plot file are, in general, non-projected GPS coordinates, according to the worldwide geodetic positioning system known as WGS84, which is the system associated with GPS-type satellite positioning. Any other type of coordinates will also be able to be processed.

Then the plot file is divided into several files known as "date files", each one associated with a date, for each one of the existing dates in said plot file. This makes it possible to take into account, when determining an optimum estimation of time lag, the influence of the date of the time lag value.

When the number of dates listed in the plot file is significant, for example, more than four, a reduced number of files is optionally selected from the date files, corresponding to a reduced number of dates.

For example, this reduced number of dates is set to a value N, and only the N dates associated with date files comprising the most recorded data are selected (that is, best covering the plot of land), the relevant N value being able to be equal to four.

Likewise, the date files representing at least a predetermined percentage of points of the farming plot are selected, for example 80%.

Finally, a set of data is created for each time lag value, amongst a set of time lags to test, for example from minus fifteen seconds to fifteen seconds.

To do this, for each set of relevant data associated with a measuring point, the geographical coordinates of this measuring point are shifted in accordance with the chosen difference, replacing the geographical coordinates of this measuring point by the geographical coordinates of the previous measuring point by a given time lag.

Eventually, a set of data known as the "set of adjusted data" is obtained for each one of the chosen difference values and for each one of the dates.

Figure 4:
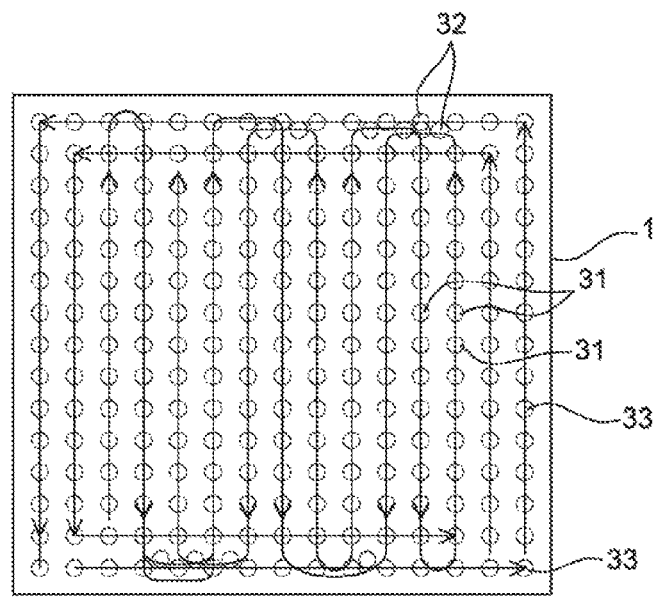
FIG. 4: a diagram illustrating the paths of a farming machine over a plot and measuring points, relevant or not.

In a step 220 (illustrated by FIG. 4), a set of adjusted data is used and, in this set of adjusted data, measuring points known as "normal measuring points", are selected.

The normal measuring points are, for example, made up of measuring points 31 positioned on substantially straight rows of lines parallel to each other. The ideal is to have rows where the directions of travel are opposed (because, as been seen, in this case, the positioning errors of the measurements relations to the time difference are added up).

These normal measuring points are indeed considered to be the most relevant for seeking the optimum estimation of the time lag, amongst all the measuring points.

Thus, typically, the measuring points located at the start and end of row 32, at the half-turns as well as measuring points constituting the identification 33 of the plots are not relevant for determining an optimum estimation of the time lag. They are therefore excluded from the set of normal measuring points.

These normal measuring points are identified automatically, for example according to a dedicated algorithm.

The normal measuring points 31, thus determined, are then optionally projected on a regular-mesh grid, the associated data (grain weight, moisture etc.) being interpolated by linear regression.

Thus a set of meshed points 31' is obtained, regularly distributed according to a predetermined grid over a representation of the plot of land 1, these meshed points representing interpolated measuring points, associated with data, also interpolated.

This step facilitates calculation of areas thereafter.

Preferentially, an optionally weighted flow map is thus built, constituting a matrix of meshed points for mapping the farming plot according to a consistent geometric distribution. Unlike measuring points the position of which comprises a random part (linked, for example, to the slight differences in the path of the combine harvester 2), the meshed points are therefore distributed according to a grid, forming for example, a regular square mesh.

In a step 230, a three-dimensional meshed data map is determined from the meshed points 24, for each one of the sets of adjusted data, each set being associated with a date and a time lag value.

This three-dimensional meshed data map is defined in Cartesian coordinates (X, Y, Z). The coordinates X, Y of a meshed point correspond to the geographical position of the meshed point (latitude and longitude typically), the Z axis corresponds, for example, to an optionally weighted flow value associated with this meshed point.

Figure 5:
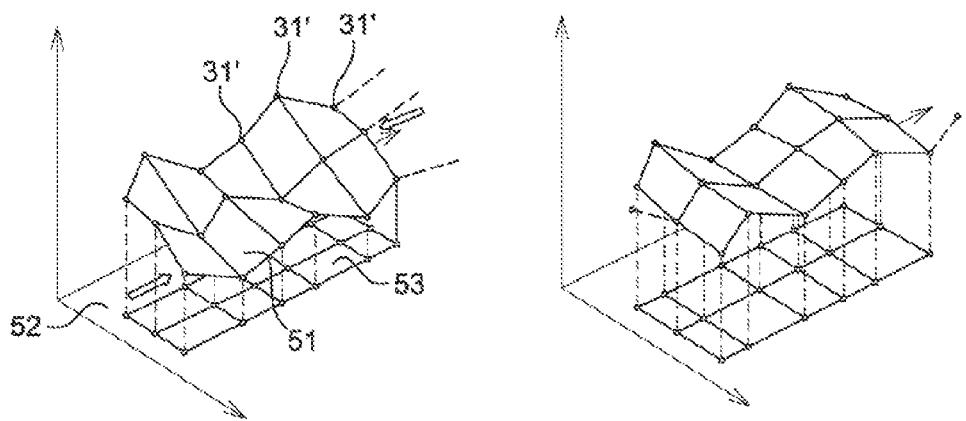
FIG. 5: a diagram illustrating the principle of estimating the difference value.

In another embodiment, the Z axis can also correspond to an optionally weighted yield value associated with this meshed point. In the example, FIG. 5 left illustrates a weighted three-dimensional flow map in a case of time lag being erroneous or null, with points very different from one to the other, and therefore located at very different "heights". On the other hand, FIG. 5 right illustrates a weighted three-dimensional flow map in a case of optimum adjustment (with an optimum estimation of the initial time lag from the measured data), with variations in height of the measuring points attenuated between nearby points.

Then an area known as "developed area" 51 is calculated from this optionally weighted three-dimensional flow map (or with an optionally weighted yield), this developed area being, for example, calculated as the sum of the area of sides which are determined by the three-dimensional yield map points.

A projection plan 52 is also defined, corresponding to a plan defined by z=0, namely here by an optionally weighted zero flow value or a optionally weighted zero yield value.

An area known as the "projected area" 53 is calculated, corresponding to the area of the projection of the optionally weighted three-dimensional flow or yield map, onto the projection map. The projected area 53 is naturally smaller than the area of the developed area 51 of this optionally weighted three-dimensional flow or yield map.

Then a "projection rate" is defined, equal to the ratio between the three-dimensional developed area 51 and the projected area 53.

This projection rate is calculated for each one of the sets of adjusted data. A set of adjusted data corresponds to an estimated time lag value.

It will be understood that an erroneous time lag leads to a spatial shift of data and leads to abrupt changes in optionally weighted flow or yield values. The misalignment of these values causes an increase of the three-dimensional developed area 51 of this optionally weighted flow or yield map in relation to the projected area 53. The ideal time lag, on the other hand, gives a developed area of this optionally weighted three-dimensional flow or yield map that is smoother and therefore less significant. The degree of projection is therefore lower for a better estimation of the time lag.

In a step 240, first of all, the time lag value corresponding to a set of adjusted data is determined, which minimizes the degree of projection.

Figure 6:
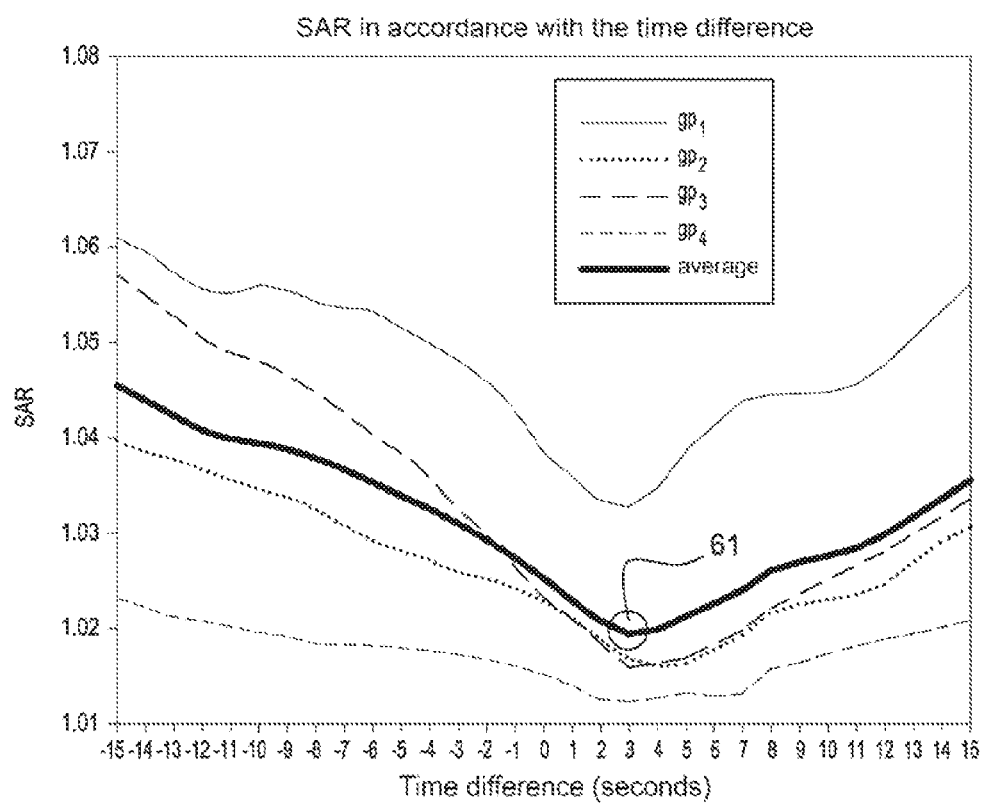
FIG. 6: a set of curves illustrating the way of determining the optimum difference value, in an example of implementation.

This value is the optimum value of the time lag for the relevant date file data associated with the date corresponding to the set of adjusted data (see FIG. 6 for which the optimum estimation of time lag is 3 seconds, corresponding to a minimum degree of projection at the point marked 61 on the figure). Therefore, here a time lag for each date is calculated.

Secondly, the date file data are adjusted with the optimum value of the time lag to supply a file known as the "corrected date file".

All of the date files constituting a plot are then re-associated. The date files for which there has been no time lag calculation, are adjusted according to the date file closest in time, and with the largest number of pieces of data.

In a step 250, the data from the corrected plot file are filtered:

by eliminating, in the data from the corrected plot file, the points which have an optionally weighted flow or yield value equal to 0, by calculating the average M of the optionally weighted flow or yield values for the remaining data (namely the measuring point with zero production value excluded), by calculating the standard deviation EC of the optionally weighted flow or yield values, and the elimination of all measuring points having an absolute flow or yield value higher than the absolute value of the average M with k times the standard deviation EC added for the flow or yield data respectively.

and by eliminating all measuring points having an optionally weighted absolute flow or yield value higher than the absolute value of the average M with k times the standard deviation EC added for the optionally weighted flow or yield data respectively. In a preferred embodiment, k=3. These points are eliminated as the associated values are considered to be abnormal.

The resulting data file is known as the "filtered plot file" in the remainder of the description.

In a third phase 300, the data contained in the filtered plot file is cleaned in order to obtained a clean, filtered, corrected plot file.

In this phase, measuring points corresponding to point 5 located outside of the farming plot are eliminated. This cleaning is carried out by entering or automatically detecting the contour of the plot.

In a particular embodiment, this contour can be calculated from a GPX-type file supplied by a GPS receiver.

In a variant, an operator, who may be the farmer himself, displays data contained in the filtered plot file using mapping software known per se, and eliminates the measuring points located outside of the farming plot.

In a phase 400, a contour called the harvested plot contour is created. This harvested plot contour is obtained by tracing an area known as a buffer equal to a cutting half-width (this cutting half-width being a piece of data associated with the combine harvester 2 in question) around each measuring point. All of the buffers are then merged and smoothed to obtain this harvested plot contour. The harvested plot contour makes it possible to evaluate as accurately as possible an area corresponding to the actually harvested area of the plot of land 1.

Once the data are corrected, filtered and cleaned, phase 500, known as the phase of creating the final yield map, is passed to.

In this phase 500, in a first step 510, the measuring data are distributed over the space covered by the width of the equipment, that is between two successive paths of the combine harvester 2 over the plot of land 1. Here, the cutting width of the farming equipment is taken into account. A single measuring point in fact corresponds to a width of cut and to a flow recorded at a given moment. That is to say the area covered by the width of cut is associated with a single measuring point.

Each one of the measuring points is then replaced by Np points, distributed homogeneously over the width of cut. In a preferred embodiment, Np is equal to five.

In a variant, it is also possible to distribute the measuring points by Nt points distributed homogeneously between two consecutive moments of measurement.

However, it should be noted that this method presents a bias because the width of cut is not always used in its entirety (case of plot edges, for example). In addition, the production of grain is not necessarily homogeneous over the area in question.

This method is necessary to distribute the flow along the cutting bar, in the absence of information about the width of cut actually used at a moment t. In a preferential method, in the case where the information about the instantaneous effective width of cut is supplied, the dispersion of the mass flow can be done over the effective width.

Thus, in a second step 520, an algorithm using a principle described by Blackmore and Marshall (1996) is used.

A grid, of predetermined mesh, is applied over the plot of land 1 (see FIG. 7A), and the flows measured inside each cell, the area of which is known, are added together. This method is called "Potential mapping".

For the plot edge cells (FIG. 7B), the percentage of area occupied by the plot of land is defined, by intersecting the harvested plot contour with the cell edges.

Then, all of the points contained in each cell (FIG. 7C) are added together. A flow or an output measured at a given frequency, i.e. one second in general, is associated with each point.

Figure 7D:
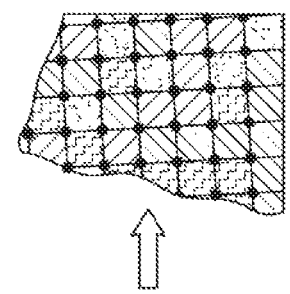
FIGS. 7A to 7D: the steps of the method of establishing a yield map.
Figure 7C:
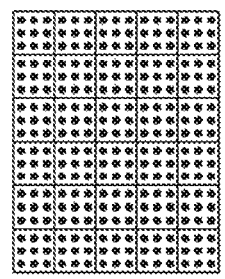
Figure 7B:
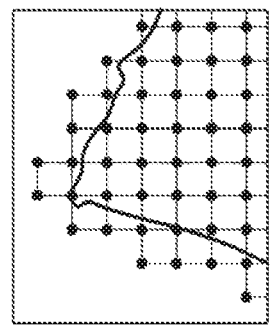
Figure 7A:
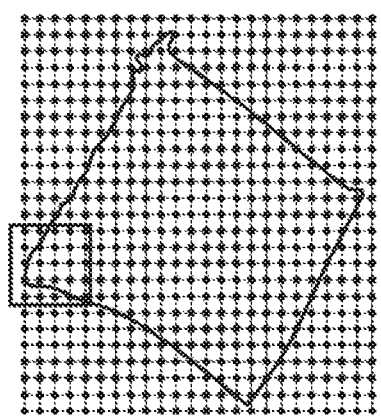

Then, the flow measured is divided by the area of the cell to obtain a yield value associated with each cell (FIG. 7D).

To obtain a grid of a predetermined first resolution, here preferentially chosen equal to thirty meters, a satellite image of the plot of land 1 is used. The geographical coordinates of the top-left point of this image, as well as the number of image pixels, and the scale of the image, allow the recreation of the nodes of the grid. The most used widths of cut being between 4 and 15 m, an established cell size, preferentially 30 m, is fully adequate for the present application. Cells of this size show a crop area requiring the combine harvester 2 to pass through several times. Consequently, the calculated yield values are based on sufficient measurements to be correct over these passings.

It is clear that these data are cited here only as a non-exhaustive example.

The following step consists of a re-sampling at five meters of the yield values obtained by interpolation by using a method known as kriging, known per se. This step smoothes the data and reveals areas of interest on the map, without being distorted by variations or abnormalities on areas too small to be able to take action, which is useful for being able to achieve an agronomical diagnosis.

In the embodiment presented here as an example, the yield map obtained is preferentially displayed with a color palette and with a series of value classifications, determined by equal intervals. This presentation clearly highlights abnormally low yield areas with regard to the plot average, which saves precious analysis time for the user.

What is claimed is:

1. A method of correcting a time lag for a set of data, comprising the steps of:
generating a plurality of adjusted data sets by replacing geographic coordinates of a measuring point supplied by a geolocation system with geographic coordinates of a previous or a future measuring point having a time lag value to shift the geographic coordinates of the measuring point; and
for each set of adjusted data:
building a three-dimensional map showing latitudes, longitudes and heights along the X, Y and Z axes, respectively, in accordance with the adjusted data associated with the measuring point, wherein a height represents a sensor value;
determining a measurement of a developed surface area of the three-dimensional map;
calculating a surface area of a projection of the three-dimensional map onto a plane of latitudes and longitudes;
calculating a projection ratio between the developed surface area of the three-dimensional map and the area of projection;
determining a minimum value of the projection ratio for the sets of adjusted data; and
correcting the set of data using the minimum value.

2. The method of claim 1, further comprising the steps of selecting, within each set of adjusted data, a set of normal measuring points comprising the measuring points positioned on substantially straight rows of lines parallel to one another; and excluding measuring points located at a start and an end of each of the rows, located at half-turns and constituting an identification of a plot of land from the set of normal measuring points.

3. The method of claim 2, further comprising the steps of projecting the normal measuring points onto a regular mesh grid; and interpolating associated data by linear regression.

4. The method claim 1, further comprising the step of filtering the corrected data using the minimum value and wherein the step of filtering further comprises the steps of: eliminating points in the corrected data having a weighted flow or yield value equal to 0; calculating an average M and standard deviation EC of flow measurements or yield values; eliminating measuring points having an absolute flow or yield value higher than the absolute value of the average M plus k times the standard deviation EC for the flow or yield data, respectively.

5. The method of claim 1, wherein the data are crop flow or yield measurements; and further comprising the step of weighing the crop flow or yield measurements from a total weight harvested from a plot of land.

6. The method of claim 1, wherein the step of generating the set of adjusted data to shift the geographic coordinates of the measuring point comprises the step of shifting values recorded by the sensor from one measuring point to another.

7. A method, comprising:
receiving a data set comprising a set of geographic coordinates defining a plurality of measuring points and sensor data collected at each of the measuring points by a vehicle moving over a plot of land, the measuring points and the sensor data being misaligned due to a time lag of unknown duration in the sensor data;
generating an adjusted data set by correcting the data set based on an optimal value for the time lag, the optimal value for the time lag being one of a plurality of candidate time values and having been determined to minimize the sensor data misalignment as compared to other candidate time lag values of the plurality of candidate time values; and generating a yield map by distributing sensor data associated with each particular measuring point of the adjusted data set across an area associated with the particular measuring point and adding the distributed sensor data to a grid of cells that is applied over a representation of the plot of land.

8. The method of claim 7, further comprising:

importing a set of raw data files generated from a complete harvesting of the plot of land;

translating the set of raw data files into a set of formatted data files in a standard format;

processing the set of formatted data files to generate a set of plot files each including information connected to a single farming plot, a single crop, and a single crop cycle.

9. The method of claim 7, wherein:

the geographic coordinates of the measuring points are determined by a global positioning system as the vehicle moves over the plot of land; and the sensor data associated with a particular measuring point is determined by at least one sensor as the sensor passes over a geographical point associated with the geographic coordinates associated with the measuring point, the at least one sensor being carried by the vehicle as the vehicle moves over the plot of land.

10. The method of claim 7, wherein the sensor data includes flow values, the method further comprising weighting the flow values measured at each measuring point in accordance with a total crop weight harvested on the plot of land.

11. The method of claim 7, wherein determining the optimal value of the time lag comprises:

generating an adjusted data set for each candidate time value by replacing the geographic coordinates of each measuring point in the data set with geographic coordinates of previous or future measuring points based on the candidate time value to shift the measuring points;

determining an amount of data misalignment for each adjusted data set; and selecting as the optimal value for the time lag a candidate time value corresponding to an adjusted data set that minimizes the amount of data misalignment.

12. The method of claim 11, wherein determining an amount of data misalignment comprises:

selecting a set of normal measuring points from the measuring points of the adjusted data set;

projecting the set of normal measuring points onto a regular mesh grid to obtain a set of meshed points;

determining a three dimensional meshed data map based on the set of meshed points;

calculating a developed area as a sum of an area of sides of a polygon defined by the three dimensional meshed data map;

calculating a projected area corresponding to an area of a projection of the three dimensional meshed data map onto projection plan defined by three dimensional meshed data map;

calculating a projection rate as a ratio between the developed area and the projected area; and defining the projection rate as a measure of the amount of data misalignment in the adjusted data set.

13. The method of claim 12, wherein the step of selecting normal measuring points includes selecting measuring points positioned on substantially straight rows of parallel lines that correspond to opposing directions of travel of the vehicle over the plot of land.

14. The method of claim 12, wherein the three dimensional meshed data map includes X,Y coordinates that define geographic locations and Z coordinates that define weighted flow values associated with each geographic coordinate.

15. The method of claim 12, wherein the three dimensional meshed data map includes X,Y coordinates that define geographic locations and Z coordinates that define weighted yield values associated with each geographic coordinate.

16. The method of claim 7, wherein a given measuring point is associated with sensor data collected across of a width of a cutting bar that is coupled to the vehicle, the method further comprising distributing sensor data over a space covered by the width of the cutting bar.

17. The method of claim 16, wherein distributing sensor data includes replacing a given measuring point with a plurality of points distributed homogenously over the width of the cutting bar.

18. The method of claim 16, wherein distributing sensor data includes replacing a given measuring point with a plurality of points distributed homogenously between two consecutive moments of measurement.

19. The method of claim 7, further comprising:

applying a grid of predetermined mesh over the representation of the plot of land;

adding together flows measured at all points inside each cell of the grid;

associating an output measured at a given frequency with each point inside each cell of the grid to define a measured flow; and dividing the measured flow by the area of the cell to obtain a yield value associated with each cell.

20. The method of claim 19, wherein the representation of the plot of land is a satellite image.

21. The method of claim 19, further comprising:

defining a percentage of area occupied by the plot of land within an edge cell by intersecting a harvested plot contour with cell edges.

22. The method of claim 21, further comprising:

creating a set of buffers by cutting a half-width around each measuring point; and merging together and smoothing the set of buffers to obtain the harvested plot contour.

* * * * *

UNITED STATES PATENT AND TRADEMARK OFFICE
CERTIFICATE OF CORRECTION

PATENT NO. : 9,972,058 B2  
APPLICATION NO. : 15/463442  
DATED : May 15, 2018  
INVENTOR(S) : Chloe Romier Page 1 of 1

It is certified that error appears in the above-identified patent and that said Letters Patent is hereby corrected as shown below:

On the Title Page

Related U.S. Application Data reads:
"Continuation of application No. 14/129,274, filed as application No. PCT/EP2012/062380 on Jun. 26, 2012, now Pat. No. 9,600,846."
Should be:
--Continuation of application No. 14/129,274, filed Dec. 24, 2013, now Pat. No. 9,600,846, which is a 371 of application No. PCT/EP2012/062380 filed on Jun. 26, 2012.--

In the Specification

Column 1, Line 63 reads:
"of and is defined"
Should be:
--of land is defined--

Signed and Sealed this
Twenty-seventh Day of November, 2018

Andrei Iancu
*Director of the United States Patent and Trademark Office*